US011207482B2

(12) United States Patent
Göbel

(10) Patent No.: US 11,207,482 B2
(45) Date of Patent: Dec. 28, 2021

(54) DEVICE AND METHOD FOR THE DYNAMICALLY SEALING OCCLUSION OR SPACE-FILLING TAMPONADE OF A HOLLOW ORGAN

(71) Applicant: Creative Balloons GmbH, Waghäusel (DE)

(72) Inventor: Fred Göbel, Wilhelmsfeld (DE)

(73) Assignee: Creative Balloons GmbH, Waghäusel (DE)

( * ) Notice: Subject to any disclaimer, the term of this patent is extended or adjusted under 35 U.S.C. 154(b) by 1005 days.

(21) Appl. No.: 15/533,151

(22) PCT Filed: Dec. 4, 2015

(86) PCT No.: PCT/IB2015/002309
§ 371 (c)(1),
(2) Date: Jun. 5, 2017

(87) PCT Pub. No.: WO2016/087930
PCT Pub. Date: Jun. 9, 2016

(65) Prior Publication Data
US 2017/0333654 A1 Nov. 23, 2017

(30) Foreign Application Priority Data

Dec. 4, 2014 (DE) ...................... 10 2014 017 872.2
Jan. 22, 2015 (DE) ...................... 10 2015 000 621.5
(Continued)

(51) Int. Cl.
*A61M 16/04* (2006.01)
*A61M 16/00* (2006.01)
(52) U.S. Cl.
CPC ...... *A61M 16/044* (2013.01); *A61M 16/0447* (2014.02); *A61M 16/0486* (2014.02); *A61M 2016/0027* (2013.01)

(58) Field of Classification Search
CPC .............. A61M 16/04; A61M 16/0443; A61M 16/0434; A61M 16/0445; A61M 16/0459;
(Continued)

(56) References Cited

U.S. PATENT DOCUMENTS 3,794,043 A * 2/1974 McGinnis ........... A61M 16/044
128/207.15
4,159,722 A * 7/1979 Walker ................ A61M 16/044
128/207.15
(Continued)

FOREIGN PATENT DOCUMENTS

WO    WO 2013/139986    9/2013

OTHER PUBLICATIONS

Badenhorst, Changes in Tracheal Cuff Pressure in Respiratory Support, Crtitical Care Medicine 15(4), 1987, pp. 300-302.
(Continued)

Primary Examiner — Samchuan C Yao
Assistant Examiner — Ned T Heffner
(74) Attorney, Agent, or Firm — Pandiscio & Pandiscio

(57) ABSTRACT

A device (1) for the tracheal intubation of and the administration of ventilation to a patient for rapid volume-compensating sealing of the trachea, wherein the sealing surfaces of a preferably fully and residually formed balloon-like film body (4) abut the wall of the trachea with a sealing pressure of the balloon (4) which is as constant as possible and follow the thoracic pressure acting on the balloon with the least possible time latency with regard to corresponding fluctuations of the balloon inflation pressure, and the trachea is kept sealed under such dynamic fluctuations or respiration synchronously alternating fluctuations of the balloon inflation pressure. This is enabled by a defined large lumen (7, 5) supply of the balloon inflation medium, the supplying lumen being measured in such a way that a sealing pressure-
(Continued)

maintaining extracorporeal volume compensation that works in a time synchronous manner can be achieved in the sealing balloon element.

17 Claims, 4 Drawing Sheets

(30) Foreign Application Priority Data

| | | | |
|---|---|---|---|
| Jan. 29, 2015 | (DE) | ................. | 10 2015 001 030.1 |
| Mar. 4, 2015 | (DE) | ................. | 10 2015 002 995.9 |
| Nov. 18, 2015 | (DE) | ................. | 10 2015 014 824.9 |

(58) Field of Classification Search
CPC ............ A61M 16/044; A61M 16/0447; A61M 16/0486

See application file for complete search history.

(56) References Cited

U.S. PATENT DOCUMENTS

| | | | | |
|---|---|---|---|---|
| 4,285,340 | A * | 8/1981 | Gezari | A61M 16/0452 |
| | | | | 128/205.24 |
| 4,649,914 | A * | 3/1987 | Kowalewski | A61M 16/044 |
| | | | | 128/207.15 |
| 4,762,129 | A * | 8/1988 | Bonzel | A61M 25/104 |
| | | | | 604/103.1 |
| 4,770,170 | A * | 9/1988 | Sato | A61M 16/044 |
| | | | | 128/205.24 |
| 5,029,591 | A | 7/1991 | Teves | |
| 5,188,592 | A * | 2/1993 | Hakki | A61M 16/0404 |
| | | | | 604/35 |
| 5,947,927 | A | 9/1999 | Mertens | |
| 6,802,317 | B2 * | 10/2004 | Gobel | A61M 16/04 |
| | | | | 128/207.14 |
| 8,393,328 | B2 * | 3/2013 | Angel | A61M 16/04 |
| | | | | 128/200.26 |
| 2007/0277830 | A1 | 12/2007 | Ladru et al. | |
| 2012/0145159 | A1 * | 6/2012 | Yamada | A61M 16/0445 |
| | | | | 128/207.15 |
| 2013/0146062 | A1 | 6/2013 | Schumacher et al. | |

OTHER PUBLICATIONS

Bassi, An In Vitro Study to Assess Determinant Features Associated With Fluid Sealing in the Design of Endotracheal Tube Cuffs and Exerted Tracheal Pressures, Critical Care Medicine 41(2), 2013, pp. 518-526.

* cited by examiner

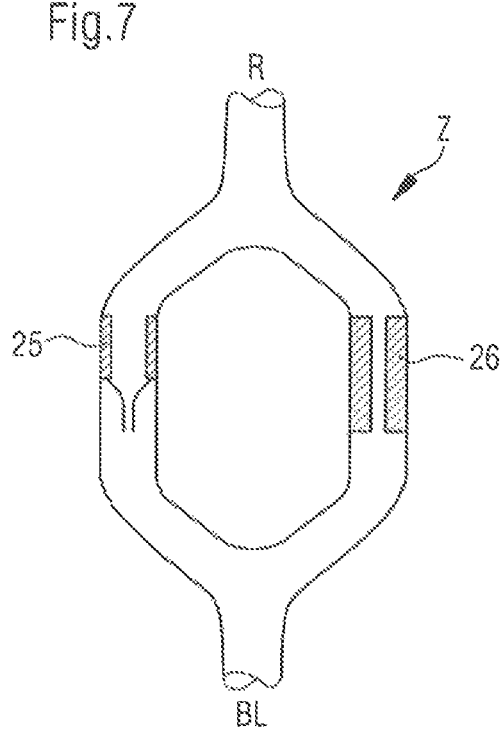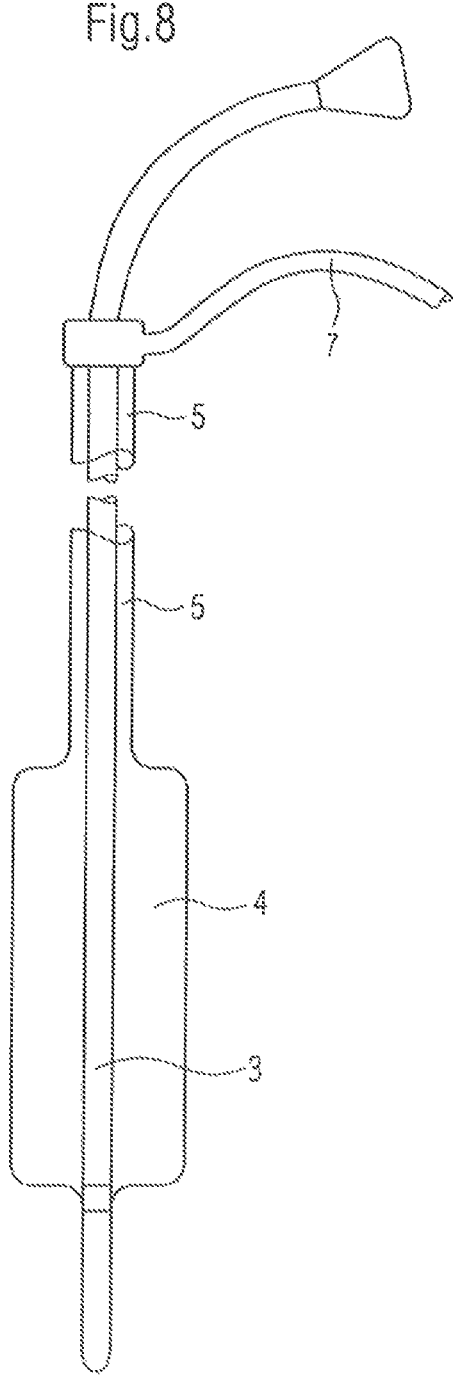

DEVICE AND METHOD FOR THE DYNAMICALLY SEALING OCCLUSION OR SPACE-FILLING TAMPONADE OF A HOLLOW ORGAN

REFERENCE TO PENDING PRIOR PATENT APPLICATIONS

This patent application claims benefit of International (PCT) Patent Application No. PCT/IB2015/002309, filed 4 Dec. 2015 by Creative Balloons GmbH for DEVICE AND METHOD FOR THE DYNAMICALLY SEALING OCCLUSION OR SPACE-FILLING TAMPONADE OF A HOLLOW ORGAN, which claims benefit of: (i) German Patent Application No. DE 10 2014 017 872.2, filed 4 Dec. 2014, (ii) German Patent Application No. DE 10 2015 000 621.5, filed 22 Jan. 2015, (iii) German Patent Application No. DE 10 2015 001 030.1, filed 29 Jan. 2015, (iv) German Patent Application No. DE 10 2015 002 995.9, filed 4 Mar. 2015 and (v) German Patent Application No. DE 10 2015 014 824.9, filed 18 Nov. 2015, which patent applications are hereby incorporated herein by reference.

FIELD OF THE INVENTION

The invention is directed to a device and a method for the dynamic occlusion or tamponade of a hollow organ by means of a balloon-like element, in particular for the dynamic, aspiration-preventing seal of the intubated trachea in patients who are breathing independently and in patients in a machine-assisted spontaneous ventilation mode.

BACKGROUND OF THE INVENTION

In many cases, the continuous motility of the organ itself is a fundamental problem associated with the sealing closure or space-filling tamponade of organs or cavities with a fillable, balloon-like element in a way that is gentle to the organ and efficient. Organs or body cavities that are limited by musculo-connective tissue often have autonomous motility or are subjected to the dynamics of adjacent organs or structures. In order to create a continuous seal of the organ lumen, autonomous or correspondingly motile organs require a particular regulating mechanism that reacts quickly to fluctuations in the organ diameter or changes in the tone of the organ wall. As the changes in diameter or tone occur, said mechanism must act as a synchronously as possible.

The problem of dynamic, synchronized adaptation of a balloon occlusion of a hollow organ can be illustrated with the example of the human trachea. The trachea is a tube-like structure with portions composed of cartilaginous tissue, connective tissue and muscle. It extends from the lower section of the larynx to the branching of the main bronchi. The front and side portions of the trachea are stabilized by clip-like, approximately horseshoe-shaped structures, which in turn are connected to each other in the longitudinal direction by connective tissue-like layers of tissue. The trachea lumen is closed off on the rear-wall side by the so-called pars membranacea, which consists of material made of continuous musculo-connective tissue, without any reinforcing cartilaginous elements. The esophagus, which is made of musculo-connective tissue, lies on its dorsal side.

The upper third of the trachea is usually located outside of the thorax, while the two lower thirds lie within the thoracic cavity delimited by the thorax and diaphragm. The lower thoracic portion of the trachea is thereby especially subjected to the pressure fluctuations in the thoracic cavity that occur as part of the thoracic respiratory mechanics of a spontaneously breathing patient as well as a patient who is spontaneously breathing with assistance.

When the patient breathes in, the thoracic volume is enlarged by the lifting of the ribs and simultaneous lowering of the diaphragm, and the intrathoracic pressure therefore decreases. As a result of respiratory mechanics, this drop in pressure leads to the inflow of inhaled air into the lungs, which expands with the increase in thoracic volume.

However, the pressure drop in the thorax associated with the increase in thoracic volume also leads to corresponding drops in pressure within filled balloon elements positioned in the patient's thorax. Balloon elements such as these are used in tracheal tubes and tracheostomy cannulas, for example, to seal the deep airways against inflowing secretions from the throat and to permit positive pressure ventilation of the patient's lungs. The cyclical drops in thoracic pressure caused by the patient's own breathing can move the sealing pressure in the balloons of ventilation catheters into low ranges, in which a sufficient seal against secretions that collect in the trachea above the sealing balloon (cuff) is no longer ensured. See Badenhorst C H, Changes in tracheal cuff pressure in respiratory support, Crit Care Med, 1987; 15/4: 300-302.

Whereas the sealing performance of conventional PVC tracheal tube cuffs correlates very closely with the effective filling pressure in the cuff, the especially thin-walled polyurethane tracheal tube cuffs demonstrate significantly more stable sealing efficiency when the tracheal sealing pressures fall into ranges around 15 mbar. See Bassi G L, Crit Care Med, 2013; 41: 518-526.

Of particular importance for the secretion seal of tracheal sealing balloons, however, is the pressure range from 5 to 15 mbar, which is easily achieved during the independent breathing of a patient, essentially from breath to breath. Seal-optimized ventilation catheters with micro-thin-walled PUR cuffs can also still ensure good sealing performance at ca. 10 mbar filling pressure. However, they cannot protect against inflowing, infectious secretions during pressure drops below 10 mbar to sub-atmospheric thoracic pressure values.

No sealing technology is yet available for sealing the trachea by means of a cuff-like sealing balloon, which synchronizes with the breathing effort of the thorax, is atraumatic, seals efficiently over sufficiently wide ranges of filling pressure and is cost-effective to manufacture. Although many different technical embodiments of filling pressure-regulating devices for tracheal ventilation catheters are described in the prior art, a sufficiently synchronized adaptation of the sealing pressure to alternating thoracic pressures, as are observed in autonomous breathing in patients, has not yet been achieved.

In the known ventilation catheters, the trachea-sealing balloon element is usually filled by small-bore filling lines which are extruded into the shaft of the catheter. The small cross-sections of the filling lines generally do not ensure a flow rate of the filling medium which fills the balloon that is sufficiently strong to maintain a tracheal seal during the drop in thoracic pressure. Even technically complicated extracorporeal control mechanisms, such as the CDR 2000 device produced by Logomed GmbH (no longer commercially available), function inadequately because of the small-bore supply lines between the sealing balloon element and the regulator.

SUMMARY OF THE INVENTION

The present invention describes a novel catheter technology that permits a quick flow rate between a regulating mechanism outside the body and a balloon-like sealing element placed in the trachea by means of an especially flow-efficient supply line for the filling medium. Technologically simple and cost-effective means are used to compensate for the cuff volume in a way that is sufficiently synchronized for the dynamic sealing of the trachea of a spontaneously breathing patient and that maintains the seal.

The invention further describes a thin-walled ventilation catheter shaft that has a single lumen and a shaft wall that is preferably stabilized by a corrugated tube-like corrugation. The corrugation of the shaft permits especially low wall thicknesses, which optimally allows for large inner lumens for the particularly low-resistance breathing of the patient. The corrugation additionally gives the shaft a particular low-tension or non-elastic axial flexibility and thus adaptability in the trachea of a spontaneously breathing patient. A flexible shaft such as this can additionally be made of especially hard PUR types, which then permit particularly thin wall thicknesses.

One possible embodiment of the invention is based on a balloon element which is fixedly and sealingly attached to the supporting shaft body at the distal end of the ventilation catheter and the proximal end of which narrows almost to the outer dimensions of the catheter shaft, but leaves a coaxial gap for the shaft. This proximal extension of the balloon can extend into the thoracic section of the trachea, but can also be guided into the extra-thoracic sections of the trachea as far as the region of the vocal cords or also to the lower region of the throat, wherein a particular free gap is formed between the sleeve of the proximal balloon segment that narrows in this way and the enclosed shaft.

The gap created in this way permits an especially large-bore, efficient volume flow between a volume reservoir disposed outside the body and the trachea-sealing balloon element. The gap further prevents potentially damaging direct contact by the corrugated catheter shaft with the epithelium of the trachea.

The concentric arrangement of the catheter shaft in a tapering, tube-like proximal balloon-segment is advantageous especially in the region of the vocal cords. Here, the balloon envelope that encloses the shaft rests against the vocal cords in a protective way and prevents abrasive effects by the shaft when it moves relative to the respiratory tract.

In the proximal section of the tracheal ventilation catheter, the end of the tube-like tapered balloon segment is preferably accommodated by a multi-lumen shaft element. This shaft element preferably has a supply line cross-section whose flow-affecting cross-section preferably corresponds to the flow-affecting cross-section of the gap between the shaft and the proximal balloon segment. A filling tube then attaches to the supply lumen integrated into the proximal catheter, said filling tube having a diameter with corresponding flow characteristics to those ensured within the catheter.

The invention shows an example of a method of calculating the dimensions of the claimed gap created between the catheter shaft and the proximal extension of the balloon end or balloon body, which provides a good approximation of how large the radial gap must be in order to achieve a sufficiently compensating volume flow between the regulator and balloon in under 10 milliseconds after thoracic pressure begins to decrease.

Both the proximal balloon segment surrounding the shaft and the distal balloon segment sealing the trachea are preferably produced from a material that is as thin-walled as possible and only slightly elastic. In this way, the required dimensional stability of the balloon body is ensured when it is loaded with filling pressure from the inside or under mechanical stress from the outside.

The invention further describes various methods for quickly sealing the trachea in a volume-compensating way, wherein a claimed catheter provided with an occluding or tamponading balloon element is connected to an extracorporeal regulator device. By coupling the catheter with the regulator, an interior space is created that can be charged with isobaric filling pressure.

The continuously flow-efficient, large-bore connection between the sealing balloon element and a volume source in which the pressure is kept constant represents the required synchronicity between the patient's thoracic respiratory activity and the volume flow that is needed to obtain the tracheal seal.

Quick shifts in volume are permitted in the claimed combination of a catheter and a regulator, e.g. by gravity- or spring-powered regulators, which function in the range of low, physiologically harmless pressures, i.e. in a pressure range of ca. 25 to 35 mbar, and do not require unphysiologically high pressure gradients that force the volume flow in order to ensure sufficient volume flows over the connecting supply line between the cuff and regulator.

The regulator can be configured according to the design described in PCT/EP/2013/056169, for instance. The present invention is preferably designed for this simple form of control by a communicating system of interior spaces under isobaric pressure in the physiological pressure range of 20 to 50, preferably 20 to 35 mbar.

The claimed optimized volume flow between the trachea-sealing balloon body and the extracorporeal regulator can also be achieved with tracheal tubes and tracheostomy cannulas of a conventional design, insofar as the supplying feed channel has a flow-affecting cross-sectional area that corresponds to a circular cross section with a circular diameter of at least 2 mm and preferably a circular diameter of 4 to 6 mm. In products with a convention design, the volume-supplying channel is usually circular and has an inner diameter of ca. 0.5 to 0.7 mm. The channel is extruded into the shaft wall of the tube shaft. It transitions outside the shaft into a tube line, which is normally connected to a one-way valve. For the purpose of the thinnest-walled shafts possible and/or in order to permit the largest possible inner diameter of the ventilation lumen, the supply lines in the shaft wall are kept correspondingly low-caliber.

The principle of flow-optimized volume compensation described above can similarly be applied to the dynamic tamponade of the esophagus of a spontaneously breathing patient. The pressure fluctuations in a tamponade balloon placed in the esophagus, which correspond to independent breathing, are usually more pronounced than in a balloon placed in the trachea. They generally conform to the prevailing absolute intrathoracic pressure. To produce a balloon tamponade in the esophagus that seals as efficiently as possible, it is proposed that the balloon be segmented so that it corresponds to the trachea. While the distal segment of the balloon, which actually seals the esophagus, extends over the extent of the esophagus between its upper and lower sphincters, a tapering balloon segment attaches in the proximal direction and optionally extends to the proximal end of the catheter supporting the balloon. The diameter ratios that are hereafter represented on the ventilation catheter and that define the resulting gap between the shaft and the proximal balloon segment can also be applied in the case of gastric tubes for nutrition and/or decompression. Here, too, the shaft of the gastric tube can consist of a single-lumen, thin-walled tube that is corrugated, entirely or in segments, to improve the bending mechanics. The connection to an isobaric volume reservoir can occur in the manner according to the invention, similarly to the tracheal tube.

BRIEF DESCRIPTION OF THE DRAWINGS

Further features, details, advantages and effects based on the invention arise from the following description of preferred embodiments of the invention and with the aid of the accompanying drawings.

FIG. 7 shows a combined valve/throttle mechanism which prevents the balloon from quickly emptying into the regulator/reservoir, which would be critical for the seal.

FIG. 8 shows a gastric tube with a proximally extended balloon segment for the dynamically sealing tamponade of the esophagus in combination with an extracorporeal isobaric volume reservoir.

DETAILED DESCRIPTION OF THE PREFERRED EMBODIMENTS

Figure 1:
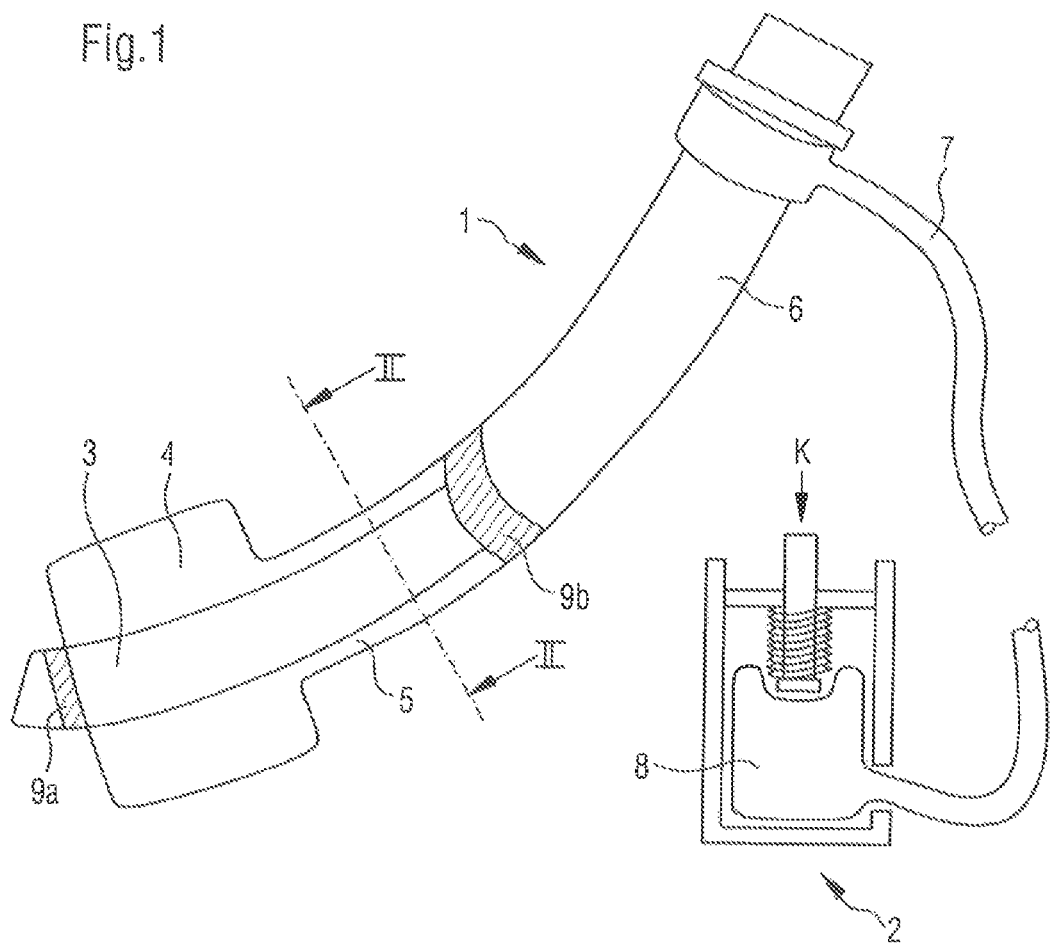
FIG. 1 shows a claimed tracheal tube in combination with an external volume-regulating device.

FIG. 1 describes, in an illustrative total overview, the communicating connection/coupling of a claimed device 1, in the form of a tracheal tube, with a preferably gravity- or spring-driven, isobaric volume reservoir 2.

The supply chamber formed by the freely communicating coupling of the tracheal tube and volume reservoir 2 consists of the trachea-sealing balloon segment 4, the tube-like tapered balloon end 5 that connects in the proximal direction, the supply lumen(s) in the proximal shaft element 6, the flexible supply line 7 to the reservoir that attaches to the shaft as well as the reservoir volume 8 of the regulator.

The distal shaft segment of the tube 3 supports a trachea-sealing balloon 4 at its distal end, said balloon being sealingly attached at its distal end 9a to the surface of the shaft. A tube-like proximal balloon segment 5, which tapers relative to the diameter of the sealing balloon segment 4, attaches to the balloon segment 4 in the proximal direction. Its proximal end locks tightly to the surface of the distal end 9b of the proximal shaft element 6.

If a decrease in intrathoracic pressure occurs during the course of inhaling (inspiration), and thus a corresponding transient widening of the tracheal cross-section, which in turn causes a corresponding drop in pressure within the balloon body placed in the trachea, volume flows from the reservoir 2 to the sealing balloon segment 4, wherein the reservoir continuously charges the volume with a defined pressure. As a result, the tracheal sealing pressure can be maintained even when the patient inhales deeply, with a possible pressure drop in the thorax and/or in the trachea-sealing balloon to sub-atmospheric levels, without relevant losses in the sealing capacity.

In a preferred embodiment, the reservoir 2 consists of a reservoir body 8, which can be configured e.g. as a balloon or bellows, and establishes a constant isobaric pressure in the supply chamber by a force K acting on the reservoir.

Crucial to achieving the smallest possible time latency between the initial widening of the tracheal cross-section or the initial reduction of the transmural thoracic forces acting on the tracheal sealing balloon and the start of a seal-creating shift of filling medium to the trachea-sealing balloon segment is, above all, the flow-affecting cross-sectional area of the gap S available the between the distal shaft segment 9 and the proximal extension 5 of the balloon.

In the following figure, the invention proposes especially advantageously dimensioned ratios of the cross-sectional area S to the cross-sectional area of the ventilation lumen ID and to the overall cross-sectional area OD of the catheter between the proximal shaft 6 and the trachea-sealing balloon segment 4.

Figure 2:
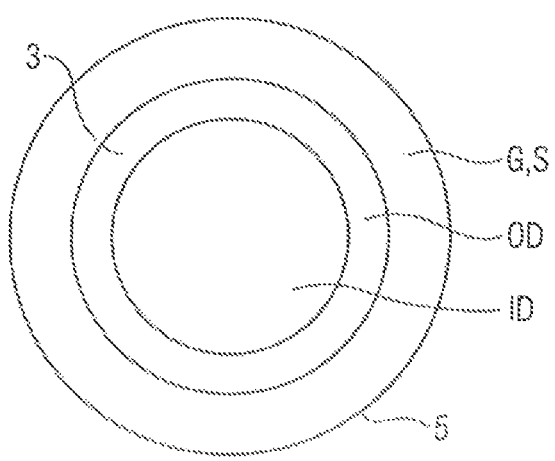
FIG. 2 shows the volume-shafting gap S relative to the overall diameter G in the vicinity of the proximal balloon extension.

FIG. 2 shows a cross-section through the volume-supplying segment 5 of the balloon of the tracheal tube pictured in FIG. 1, said segment attaching to the trachea-sealing balloon in the proximal direction.

S designates the gap surface that is preferred for the supply of filling medium to the balloon. It is defined as the difference between the cross-sectional area G, which is delimited by the sleeve wall of the supplying balloon end 5, and the cross-sectional area OD of the shaft body, which is delimited by the outer surface of the shaft. Here the cross-sectional area S should be 1/10 to 5/10 of cross-sectional area G, especially preferably 2/10 to 3/10 of cross-sectional area G.

Relative to the cross-sectional area ID of the inner lumen of the shaft body, cross-sectional area S should amount to 2/10 to 6/10 of cross-sectional area ID, especially preferably 3/10 to 4/10 of cross-sectional area ID.

In addition to air as the preferred medium, liquid media can also be used to fill the trachea-sealing system.

For the quantitative calculation of the flow conditions in the volume-conducting interior space of the balloon, in particular based on the pressure ratios in the trachea-sealing balloon segment 4, the following place-holder values should be used:

$V_i$ Volume of the distal balloon segment 4
$p_i$ Pressure in the distal balloon segment 4
$\rho_i$ Filling density in the distal balloon segment 4
$M_1$ Air mass in the distal balloon segment 4
$V_2$ Volume of the extracorporeal reservoir 8
$P_2$ Pressure in the extracorporeal reservoir 8
$\rho_2$ Filling density in the extracorporeal reservoir 8
$m_2$ Air mass in the extracorporeal reservoir 8

The following applies for air masses $m_1$, $m_2$:

$$m_1(t) = m_{1,0} + \int_{T=0}^{T=t} S_{m,1}(T) dT \quad (1)$$

$$m_2(t) = m_{2,0} - \int_{T=0}^{T=t} S_{m,2}(T) dT \quad (2)$$

$S_{m,v}$ stands for the air flow to the respective balloon 4, 8 as an air mass flow.

According to the Hagen-Poiseuille equation, the following is true for the mass fluid flow through a line with a circular cross-section and with an inner radius R and length l:

$$S_{m,1} = \frac{\rho_1 \cdot \pi (p_2 - p_1) \cdot R^4}{8\eta \cdot l} \quad (3a)$$

$$S_{m,2} = \frac{\rho_2 \cdot \pi (p_1 - p_2) \cdot R^4}{8\eta \cdot l} \quad (3b)$$

If, however—as in this case—the secondary lumen represents an annular structure around a primary lumen, then the Hagen-Poiseuille formula does not exactly apply.

Instead, one must consider a space with a strip-like cross-section, which can ideally be imagined in a straightened form, i.e. having a flat structure or a rectangular cross-section with length L and thickness D, i.e. with a cross-sectional area $Q = L \cdot D$.

Between two plates at a distance D, the following applies for the distribution of the flow rate $v(x)$ along a direction x perpendicular to the plates:

$$v(x) = \frac{(p_1 - p_2) \cdot (D^2/4 - x^2)}{2\eta \cdot l} \quad (4)$$

This is a parabolic curve. By integration over cross-sectional area Q, the mass flowing through cross-sectional area Q during time t can be determined:

$$S_{m,1} = \frac{\rho_1 \cdot (p_2 - p_1) \cdot L \cdot D^3}{12\eta \cdot l} \quad (5a)$$

$$S_{m,2} = \frac{\rho_2 \cdot (p_1 - p_2) \cdot L \cdot D^3}{12\eta \cdot l} \quad (5b)$$

In any case, these formulas replace the above Hagen-Poiseuille formulas (3a) and (3b) for annular balloon segment 5.

Here $\eta$ stands for the dynamic viscosity of the flowing gas. For air:
$\eta$ is 17.1 µPa·s at 273 K.

Furthermore, because of the thermal equation of state of ideal gases, the following applies in the balloon 4:

$$\eta_1 = \rho_1 \cdot R_S \cdot T_1 \quad (6a)$$

and in balloon 8:

$$\eta_2 = \rho_2 \cdot R_S \cdot T_2. \quad (6b)$$

In this case, $R_S$ is the individual or specific gas constant, which for air has the value 287.058 J/(kg*K).

$T_v$ is the temperature in balloon sections 4 and 5 and in the balloon 8.

For a temperature of 23° C. or 296 K, the factor $$k = R_{S,air} \cdot T_{23°\,C.} = 85 \cdot 10^3 J/(kg \cdot K) \quad (7)$$

It should be assumed hereafter that the temperature both in balloon 4 and in balloon 8 is a constant 23° C.:

$$T_1 = T_2 = 296\ K.$$

Then the following applies:

$$p_1 = \rho_1 \cdot k \quad (8)$$

$$p_2 = \rho_2 \cdot k \quad (9)$$

Thus by inserting equation (5a) into equation (1), the result is:

$$m_1(t) = m_{1,0} + \int_{T=0}^{T=t} \frac{\rho_1 \cdot L \cdot D^3}{12\eta \cdot l}(p_2 - p_1) d_T \quad (10)$$

With equation (8), it follows that:

$$m_1(t) = m_{1,0} + \int_{T=0}^{T=t} \frac{\rho_1 \cdot L \cdot D^3}{12\eta \cdot l \cdot k} p_1 (p_2 - p_1) d_T \quad (11)$$

Moreover, the following applies in balloon 4:

$$\frac{m_1}{V_1} = \rho_1 = \frac{p_1}{k} \quad (12)$$

Therefore, the following can be written in equation (11) for mass $m^1$:

$$m_1 = \frac{V_1 \cdot p_1}{k} \quad (13)$$

The result:

$$\frac{V_1}{k} \cdot p_1(t) = \frac{V_1}{k} \cdot p_{1,0} - \int_{T=0}^{T=t} \frac{L \cdot D^3}{12\eta \cdot l \cdot k} \cdot [p_1^2 - p_1 p_2] d_T \quad (14)$$

The entire equation can be shorted to $V_1/k$. A differentiation on both sides results in:

$$\frac{dp_1}{dt} = -\frac{L \cdot D^3}{12 V_1 \eta l} \cdot [p_1^2 - p_1 p_2] \quad (15)$$

This is a Bernoulli differential equation in the form:

$$x' = -a \cdot x \cdot (x - b), \quad (16)$$

wherein $$a = \frac{L \cdot D^3}{12 V_1 \eta l} \quad (17)$$

$$b = p_2 \quad (18)$$

Hereafter it should be assumed that balloon 8 is significantly larger than balloon 4:

$$V_2 >> V_1.$$

From this it follows that the pressure $p_2$ in balloon 8 remains nearly constant, even when pressure $p_1$ in balloon 4 briefly changes. Under this assumption, the coefficients a and b from Bernoulli differential equation (16) are constant, and the solution to the Bernoulli differential equation is:

$$x(t) = \frac{b}{1 - e^{-abt - bc_1}} \quad (19)$$

The constant of integration $c_1$ can be determined as follows:

$$p_1(t) = \frac{p_2}{1 - e^{-ap_2 t - p_2 c_1}} \quad (20)$$

For t=0, the following must apply:

$$P_1(t) = p_{1,0} \quad (21)$$

The result:

$$p_{1,0} = \frac{p_2}{1 - e^{-p_2 c_1}} \quad (22)$$

$$\frac{p_2}{p_{1,0}} = 1 - e^{-p_2 c_1} \quad (23)$$

$$e^{-p_2 c_1} = \frac{p_{1,0} - p_2}{p_{1,0}} \quad (24)$$

$$-p_2 c_1 = \ln \frac{p_{1,0} - p_2}{p_{1,0}} \quad (25)$$

$$c_1 = -\frac{1}{p_2} \cdot \ln \frac{p_{1,0} - p_2}{p_{1,0}} = \frac{1}{p_2} \cdot \ln \frac{p_{1,0}}{p_{1,0} - p_2} \quad (26)$$

Inserted into equation (2), this provides:

$$\frac{p_1(t)}{p_{1,0}} = \frac{p_2}{p_{1,0} - [p_{1,0} - p_2] \cdot e^{-(\pi R^4 p_2 t)/(8 V_1 \eta l)}} \quad (27)$$

This equation is in the form:

$$\frac{p_1(t)}{p_{1,0}} = \frac{p_2}{p_{1,0} - [p_{1,0} - p_2] \cdot e^{-t/\tau}} \quad (28)$$

where $$\tau = (12 \cdot V_1 \cdot \eta \cdot 1)/(L \cdot D^3 \cdot p_2) \quad (29)$$

The following applies for minor pressure fluctuations in balloon 4, for example:

$$P_{1,0} \approx 0.9 p_2$$

Moreover, for t=T:

$$e^{-t/\tau} = e^{-1} \approx 0.368 = k_1.$$

Additionally, for t=2τ:

$$e^{-t/\tau} = e^{-2} \approx 0.135 = k_2.$$

And for t=4τ:

$$e^{-t/\tau} = e^{-4} \approx 0.018 = k_4.$$

In equation (28) this yields:

$$\frac{p_1(t = vT)}{0.9 p_2} = \frac{p_2}{0.9 p_2 - (0.9 p_2 - p_2) \cdot k_v}$$

and:

$$\frac{p_1(t = vT)}{0.9 p_2} = \frac{p_2}{(0.9 + 0.1 \cdot k_v) \cdot p_2}$$

The result:

$$p_1(t = T) = p_2 \cdot \frac{0.9}{0.9 + 0.1 \cdot 0.368} \approx 0.96 \cdot p_2$$

The control deviation of approximately $0.04 \cdot p_2$ remaining after t=τ corresponds to 40% of the initial deviation of $0.10 \cdot p_2$.

$$p_1(t = 2T) = p_2 \cdot \frac{0.9}{0.9 + 0.1 \cdot 0.135} \approx 0.98 \cdot p_2$$

The control deviation of approximately $0.02 \cdot p_2$ remaining after t=2τ corresponds to 20% of the initial deviation of $0.10 \cdot p_2$.

$$p_1(t = 4T) = p_2 \cdot \frac{0.9}{0.9 + 0.1 \cdot 0.018} \approx 0.99 \cdot p_2$$

The control deviation of approximately $0.01 \cdot p_2$ remaining after t=4τ corresponds to 10% of the initial deviation of $0.10 \cdot p_2$.

When applied within the framework of thoracic respiration, it should be noted that a breathing cycle lasts about 3 sec. So that the cuff does not become leaky over the course of a thoracic breathing cycle, this compensation time should be $t_a = vT = 20$ ms, wherein, with the parameter v, it is possible to choose how good the compensation should be after 20 ms.

This results in T=20 ms/v.

The minimal result to be sought for v=1 and $t_a = 20$ is provided as follows:

From this comes:

$$T = 20 \cdot 10^{-3} s = \frac{12 \cdot 5 \cdot 10^{-6} m^3 \cdot 0.2 \, m \cdot 17.1 \cdot 10^{-6} Pas}{L \cdot D^3 \cdot 10^5 Pa}$$

In the process, it was assumed:
$V_1 = 5$ cm$^3$
$l = 20$ cm
$p_2 = 10^5$ Pa
This results in:

$$L \cdot D^3 = 10.26 \cdot 10^{-14} m^4.$$

It should hereafter further be assumed that, at most, an interior opening with a maximum diameter of 10 mm, corresponding to a radius of 5 mm, is available in the tracheal tube. If one further disregards the cross-section of the outer surface of tube 3 and balloon 4, then the secondary lumen extends a maximum distance outward, and a medium radius $R_m$ of e.g. 4.8 mm can thus be assumed. From this, it is possible to calculate a circumferential length $L_m = 2 \pi \cdot R_m$ of approximately 30 mm=$30 \cdot 10^{-3}$ m, and from this results:

$$D^3 = 10.26 * 10^{-14} m^4 / L$$

and:

$$D^3 = 102.6 \cdot 10^{-12} m^3 / 30$$

$$D^3 = 3.42 \cdot 10^{-12} m^3$$

$$D = 1.5 \cdot 10^{-4} m = 0.15 \text{ mm}.$$

The secondary lumen thus has a cross-sectional area $Q_2$ of $Q_2 = L \cdot D = 30 \text{ mm} \cdot 0.15 \text{ mm} = 4.5 \text{ mm}^2$.

For cross-sectional area $Q_1$ of the primary lumen, D can be subtracted from the 5 mm maximum radius of the tracheal tube, and the result is 4.8 mm. This corresponds to a cross-sectional area $Q_1$ of $Q_1 = 4.85 \text{ mm} \cdot 4.85 \text{ mm} \cdot 3.14 = 74 \text{ mm}^2$.

The overall free cross-section $Q = Q_1 + Q_2 = 78.5 \text{ mm}^2$. This means:

$Q_2/Q = Q_2/(Q_1 + Q_2) = 4.5/78.5 = 0.06$.

If a shorter compensation time or better compensation within this compensation time $t_a$ is required, then more stringent requirements arise for the above ratio. Accordingly, the value of 0.06 represents the absolute lower limit, which should never be undercut because this would threaten aspiration. In order to have a safety reserve, at least the following should be selected:

$Q_2/Q = Q_2/(Q_1 + Q_2) \geq 0.08$.

Moreover, the extracorporeal supply line 7 was likewise disregarded in the above calculation, although its contribution to flow resistance is not insignificant. It is therefore recommended:

$Q_2/Q = Q_2/(Q_1 + Q_2) \geq 0.10$.

If, on the other hand, one sets v=4 and $t_a$=10 ms (i.e. the requirement that the remaining control deviation should be less than 10% after 10 ms), then the following is obtained:

$$T = 10 \text{ ms}/4 = 25 \cdot 10^{-4} \text{s} = \frac{12 \cdot 5 \cdot 10^{-6} \text{m}^3 \cdot 0.2 \text{ m} \cdot 17.1 \cdot 10^{-6} Pas}{L \cdot D^3 \cdot 10^5 \text{Pa}}$$

This then results in:

$L \cdot D^3 = 82.08 \cdot 10^{-14} m^4$, $D^3 = 82.08 \cdot 10^{-14} m^4/L$ or, when L=30 mm:

$D^3 = 27.4 \cdot 10^{-12} m^3$ $D = 3 \cdot 10^{-4} m = 0.3$ mm.

The secondary lumen thus has a cross-sectional area $Q_2$ of $Q_2 = L \cdot D = 30 \text{ mm} \cdot 0.3 \text{ mm} = 9 \text{ mm}^2$.

For the cross-sectional area $Q_1$ of the primary lumen, D can be subtracted from the 5 mm maximum radius of the tracheal tube, and the result is then 4.6 mm. This corresponds to a cross-sectional area $Q_1$ of $Q_1 = 4.6 \text{ mm} \cdot 4.6 \text{ mm} \cdot 3.14 = 66 \text{ mm}^2$.

The overall free cross-section $Q = Q_1 + Q_2 = 75 \text{ mm}^2$. This means:

$Q_2/Q = Q_2/(Q_1 + Q_2) = 9/75 = 0.12$.

Figure 3:
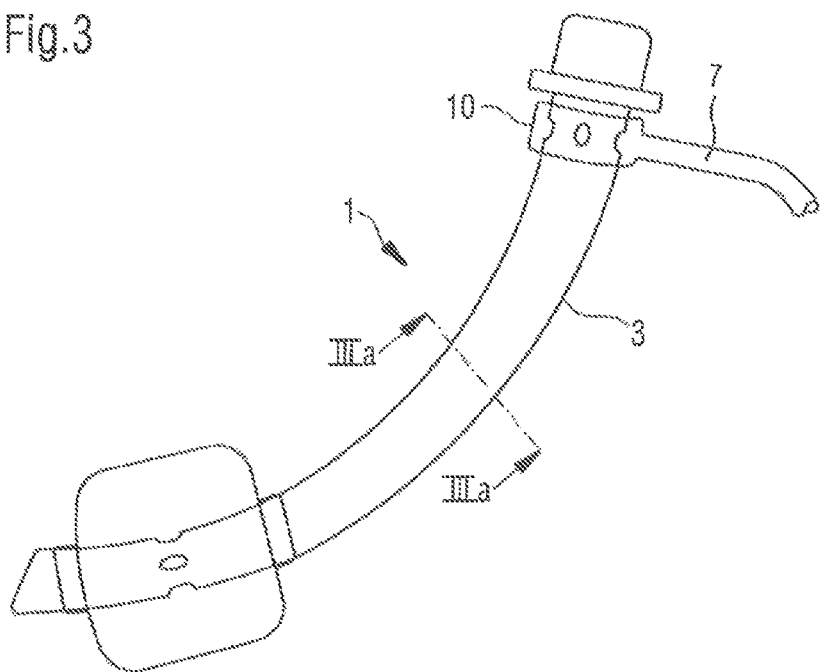
FIG. 3 shows a tracheal tube with multiple volume-shifting supply lines arranged in or on the catheter shaft.

FIG. 3 describes an embodiment of the shaft body 3 that is integrated into the shaft wall, has one or more volume-supplying channels with a volume-shifting overall cross-section that corresponds in its flow mechanics with the ratios represented in FIG. 2. Here the shaft body preferably consists of multi-lumen extruded tube material which, in addition to a central lumen for ventilation, contains supply lumens disposed around said central lumen. In one such multi-lumen embodiment, the individual lumens can be bundled or combined at the proximal shaft end by an annular structure 10.

Figure 3A:
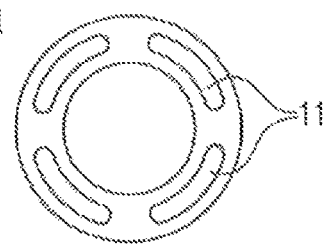
FIG. 3a shows a cross-section of the supplying, shaft-integrated lumens of the tube described in FIG. 3.

FIG. 3a shows an illustrative shaft cross-section with multi-lumen volume supply lines 11.

Figure 4:
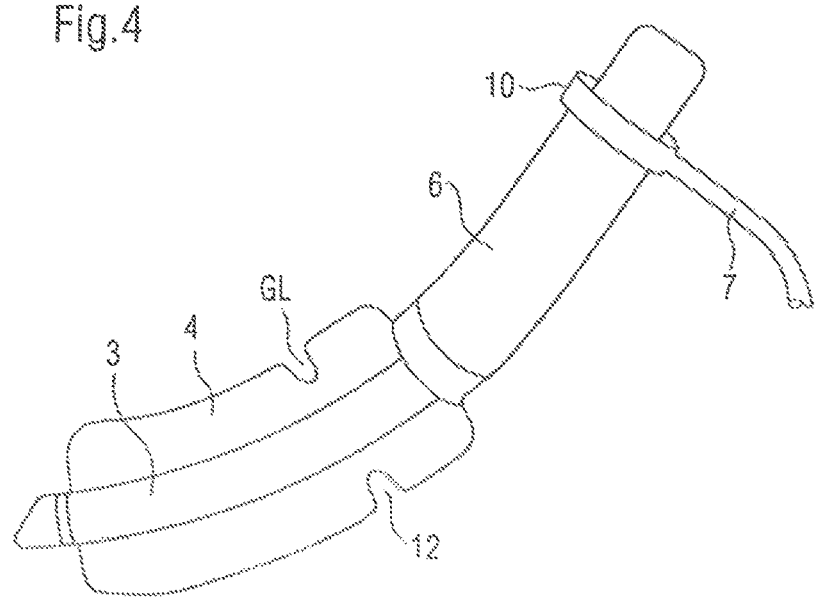
FIG. 4 shows a particular embodiment of the tube shown in FIG. 1, in which the trachea-sealing balloon extends beyond the glottis plane.

FIG. 4 shows an embodiment variant in which the trachea-sealing balloon segment 4 is extended proximally up to or beyond the plane of the vocal folds GL. This embodiment, in which the balloon segment that is elongated in this way protrudes proportionally from the thorax and is thus not exposed to fluctuations in thoracic pressure, permits an especially large balloon volume that is capable of developing a pressure-receiving buffer effect when a reduction in transmural force on the balloon, caused by breathing mechanics, occurs in the distal, tracheal segment of the balloon. The volume reserve created in this way also has a partial buffering effect when no external volume-compensating unit is connected to the tracheal tube.

In addition, owing to the large contact surface with the exposed tracheal, glottic and supraglottic mucous membranes, a maximally elongated migration path for secretions and pathogens contained therein is created.

To facilitate the trans-glottic positioning of the tube, the balloon can be provided with a circular constriction 12 in the region of the vocal cords GL. This constriction additionally allows for the free movement of the vocal folds, largely independent of the prevailing filling pressure in the balloon.

The distal shaft segment is preferably configured as a thin-walled, single-lumen tube that is stabilized by a corrugation in the shaft wall. The distal shaft transitions in the proximal direction into a shaft segment 6 that, as described in FIG. 1, allows for a large-bore supply line to the proximal balloon segment 5. In a preferred embodiment, as described in FIG. 3a, the shaft 6 is designed with a multi-lumen profile. The multi-lumen shaft segment 6 is configured to be stable enough to serve as a bite guard, which prevents a lumen-sealing closure of the ventilation lumen.

The supplying lumens that are integrated into the shaft 6 can be bundled by a terminal element 10 at the proximal end of the tube. In turn, the connection element 7 is attached to a reservoir with a sufficiently large-bore connection.

The thin-walled, single-lumen shaft body 3 is equipped with a wavy corrugation to stabilize the shaft lumen and to permit the largely tension-free axial bending of the shaft. In the preferred embodiment, it should be possible in this way to bend the shaft from 90 to 135 degrees without relevant lumen constriction and without elastic restoring forces acting upon the tissue.

For inner shaft diameters of 7 to 10 mm in the combination of a wall thickness of ca. 0.4 mm, a Shore hardness value of 95A, a peak-to-peak wave distance of 0.5 mm and a wave amplitude of 0.75 mm, it is possible to produce a correspondingly kink-resistant lumen- and flow-optimized shaft.

In the case of the corrugated embodiment of the shaft 3, when an exchangeable inner cannula is used, such as those that are conventional in tracheostomy cannulas, it is possible to use an inner cannula with a congruently corrugated profile with a corrugation that optimally conforms to the corrugation of the outer cannula and advantageously stabilizes the outer cannula.

Figure 5:
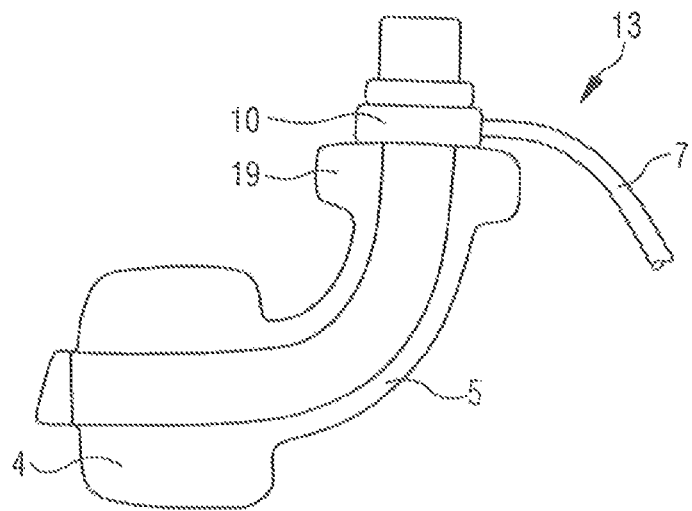
FIG. 5 shows an illustrative embodiment of a claimed tracheostomy cannula.

FIG. 5 shows an illustrative application of the flow-optimized embodiment of the supplying lumen to the trachea-sealing balloon element 4 in a tracheostomy cannula 13. Similar to the embodiment of tracheal tubes, the volume-supplying balloon end 5 here is led to the surgically created stoma to the trachea and applied to a connector 10 below the cannula flange. The cross-sectional area G of the supplying end 5 can be selected such that, beyond the claimed requirements of a fast volume flow, it is suitable to seal the stoma and thus prevent the escape of secretions. The proximal balloon end 19 can also advantageously be configured as a bulge-like widening, which lies sealingly against the stoma directly below the cannula flange.

Figure 6:
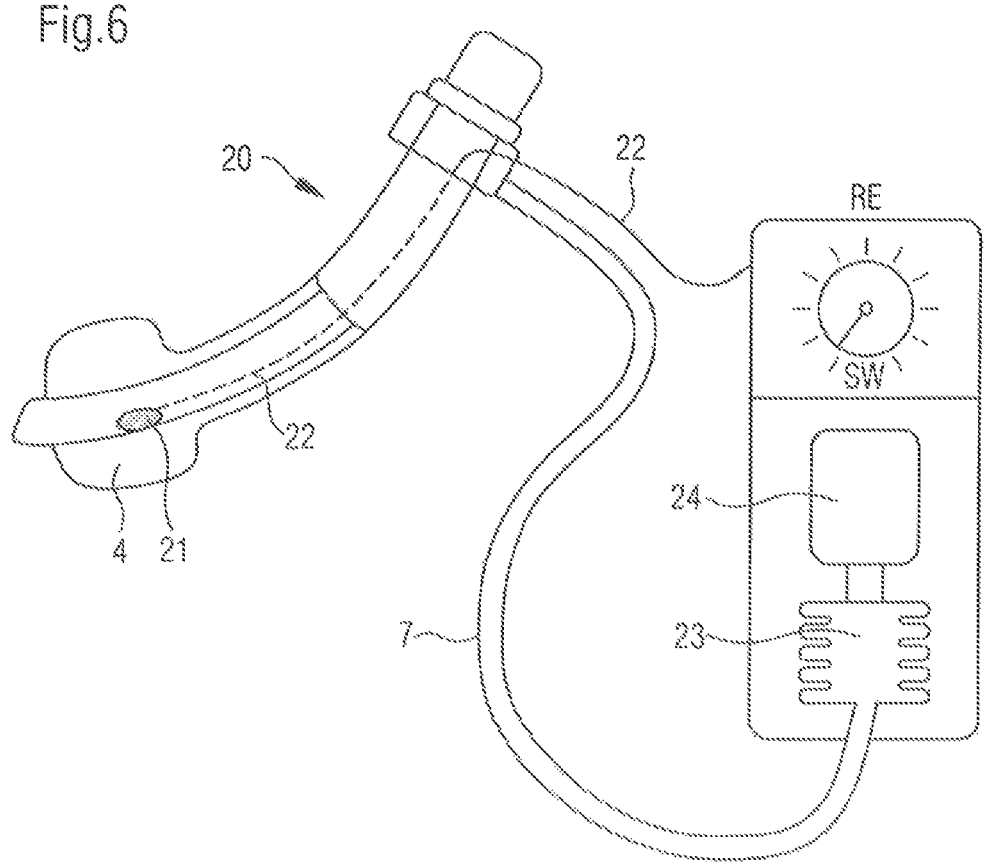
FIG. 6 shows a claimed tracheal tube with a sensor element in the region of the trachea-sealing balloon segment and a regulator unit that is arranged with a sensor in a control loop.

FIG. 6 shows a tracheal tube 20, which is provided in the region of the trachea-sealing balloon segment 4 with a pressure-sensitive or pressure-measuring sensor element 21. In a preferred embodiment, the pressure sensor is an electronic component that relays its measurement signal to an electronically controlled regulator RE via a cable line 22. The sensor element preferably consists of an absolute pressure sensor. For example, sensors based on strain gauges or piezoelectric sensors can be used. The regulator RE has a bellows-like or piston-like reservoir 23, for example, which is actuated by a drive 24 and either shifts volume to the balloon 4 or removes volume from the balloon 4; the drive can consist of a step motor or can be configured as a linear magnetic drive. The control of the regulator RE is designed such that immediate compensation can be made for deviations in filling pressure in the region of the sealing balloon segment 4 by a corresponding volume shift, or the filling pressure can be kept constant at a setpoint value SW, which can be adjusted with the regulator. In this method, the sealing balloon pressure is stabilized at a point before a mechanical breath commences and before an actual volume flow of breathing gas into the patient's lungs. This is relevant especially in patients who, for example, must expend increased breathing effort after a long period of controlled machine-assisted ventilation in order to stretch an insufficiently elastic lung in the thorax to a point that triggers a volume flow of breathing air into the lung.

In this phase of the "isometric" tension of the lung within the thorax and thus of the accompanying decrease in pressure within the thorax, drops in the filling pressure of the balloon can occur which are critical to the seal. In clinically apneic patients, i.e. patients who can perform (isometric) breathing but do not produce a perceptible breathing gas stream, the described sensor technology also makes it possible to ensure intubation in a manner that prevents aspiration.

If sudden pressure fluctuations occur in the balloon, such as when the patient changes positions or suffers a coughing attack, the control loop described can likewise efficiently and quickly shift volume to the sealing balloon or remove volume from it.

In contrast to a regulating reservoir 2, like the one described in FIG. 1 which provides a compensating reserve volume at an isobaric pressure of preferably 20 to 35 mbar, in the electronic regulation within the pressure-generating element 22 of the regulator RE it is possible to build up pressure that briefly exceeds the tracheally uncritical sealing pressure of 20 to 35 mbar and thereby accelerate the volume flow toward the sealing balloon by means of a corresponding transient pressure gradient. The continuous measurement function of the sensor thereby ensures that the pressure in the balloon does not reach critical levels.

FIG. 7. In order to avoid larger deflations of the tracheal balloon segment or balloon into the reservoir, which would be critical for the seal, such as those that can occur when the patient coughs or clenches, the connecting supply line Z between the balloon and the regulator can be provided with a large-bore, flow-directing valve 25, which prevents the backflow of filling medium from the balloon BL to the reservoir R. A throttle element 26 that is not flow-directing is arranged in parallel thereto to permit the slow exchange of volume between the balloon and reservoir.

FIG. 8 shows a similar application of the described dynamic tamponade, which allows a patient's esophagus to be sealingly closed by means of a fillable balloon element. The sealing balloon segment 4 transitions to a proximally elongated constriction 5 that defines a free gap S in the direction of the shaft element 3 for the flow-efficient shifting of a filling medium. The proximal elongation 5 of the balloon body optionally extends to or beyond the height of the mouth or nose placement. The elongation 5 transitions into a tube line 7 that is configured for an efficient flow and that, in turn, is coupled to a claimed reservoir or is connected to a different claimed regulating mechanism.

With the devices described in the preceding figures for the flow-optimized shift of volume between a trachea- or esophagus-sealing balloon 4 and an extracorporeal regulating reservoir 2, seal-creating volume compensations can take place within a tracheal or esophageal balloon body within 10 to 30 milliseconds, preferably within 10 to 15 milliseconds, after the beginning of a change in intrathoracic pressure.

LIST OF REFERENCE SIGNS

1 Device
2 Reservoir
3 Tube
4 Balloon
5 Proximal tapered balloon end
6 Proximal shaft element
7 Extracorporeal supply line
8 Reservoir volume
9a Distal tube end
9b Proximal tube end
10 Annular structure
11 Volume supply line
12 Constriction
13 Tracheostomy cannula
19 Proximal balloon end
20 Tracheal tube
21 Sensor element
22 Cable line
23 Reservoir
24 Drive
25 Flow-straightening valve
26 Throttle element
K Force
G Cross-sectional area
S Gap
ID Inner cross-section of the tube
OD Outer cross-section of the tube
GL Vocal fold plane
RE Regulator
SW Setpoint value
BL Balloon
R Reservoir

The invention claimed is:

1. A device for the dynamically sealing intubation of a hollow organ, comprising a tube in the form of a shaft that can be inserted into the hollow organ, with a primary lumen to provide access through or to the hollow organ in question, and comprising an intracorporeal sealing balloon, which surrounds a distal region of the shaft of said tube in the manner of a cuff for the purpose of sealing it against the hollow organ, wherein one or more secondary lumens for filling said intracorporeal sealing balloon are integrated into the wall of at least a proximal region of said shaft, wherein, within each cross-sectional plane that is intersected perpendicularly by the local longitudinal direction of the device, the following applies for the overall interior cross-section Q1 of the primary lumen and the sum Q2 of the interior cross-sections of all secondary lumens:

$$Q2/(Q1+Q2) \geq 0.06,$$

wherein a connection for an extracorporeal filling tube, which connection communicates with all secondary lumens, is provided at a proximal end of the tube, and wherein, in said extracorporeal filling tube,
a) a one-way valve is disposed which permits a flow in case of a pressure gradient from an extracorporeal reservoir balloon, which is or can be connected to the extracorporeal filling tube, in a direction toward the intracorporeal sealing balloon, but not in the opposite direction, and
b) a flow constriction is arranged which permits only a limited flow in every flow direction,
wherein the one-way valve and the flow constriction are arranged in parallel.

2. The device according to claim 1, characterized in that the proximal region of said shaft comprises a tubular shaft element, wherein the intracorporeal sealing balloon or a proximal region of the intracorporeal sealing balloon ends at an end face of said tubular shaft element consisting of a tube material, in which the primary lumen continues as an interior opening radially within said tubular shaft element, while the one or more secondary lumens continue in the form of one or more channels molded into the tube material of said tubular shaft element.

3. The device according to claim 2, characterized in that the minimal overall cross-section of all channels molded into the tube material of said tubular shaft element as the one or more secondary lumens is greater than or equal to the maximum cross-section of an annular secondary lumen in the proximal region of the balloon.

4. The device according to claim 1, characterized in that an annular structure acting as a collecting channel, with which all secondary lumens communicate, is located in a region of the proximal end of the tube.

5. The device according to claim 4, characterized in that the connector for the extracorporeal filling tube, which communicates with all secondary lumens, is provided on the annular structure acting as the collecting channel.

6. The device according to claim 1, characterized in that the pressure in the extracorporeal reservoir balloon is actively controlled or regulated.

7. The device according to claim 6, characterized in that the pressure in the extracorporeal reservoir balloon is actively regulated such that the pressure in the intracorporeal sealing balloon is kept constant.

8. The device according to claim 7, characterized in that the pressure in the intracorporeal sealing balloon is measured and serves as an actual value for a control loop, which exerts an influence on the pressure in the extracorporeal reservoir balloon.

9. The device according to claim 1, characterized in that, within each cross-sectional plane that is intersected perpendicularly by the local longitudinal direction of the device, the following applies for the overall interior cross-section Q1 of the primary lumen and the sum Q2 of the interior cross-sections of all secondary lumens:

$$Q2/(Q1+Q2) \geq 0.08,$$

or $$Q2/(Q1+Q2) \geq 0.10,$$

or $$Q2/(Q1+Q2) \geq 0.12.$$

10. The device according to claim 1, characterized in that the intracorporeal sealing balloon has a radially widened distal region for making a seal and a proximal region, which adjoins the distal region and tapers radially relative to it, as an envelope for the secondary lumen(s) for filling the distal sealing region.

11. The device according to claim 1, characterized in that the intracorporeal sealing balloon is performed with different outer diameters in its distal and proximal regions.

12. The device according to claim 1, characterized in that, in a proximal region of the intracorporeal sealing balloon, only one secondary lumen is provided which concentrically externally surrounds the primary lumen.

13. The device according to claim 1, characterized in that a proximal region of the intracorporeal sealing balloon does not extend all the way to the proximal end of the tube but ends before that.

14. The device according to claim 1, characterized in that the extracorporeal reservoir balloon has a larger volume in its freely deployed state than the intracorporeal sealing balloon in the distal region of the shaft of the tube.

15. The device according to claim 1, characterized in that the extracorporeal reservoir balloon is charged with a constant or near-constant pressure, for instance by a weight or a spring element.

16. A method for the dynamically sealing intubation of a hollow organ, the method comprising inserting a device into the hollow organ, the device comprising a tube in the form of a shaft that can be inserted into the hollow organ, with a primary lumen to provide access through or to the hollow organ in question, and comprising an intracorporeal sealing balloon, which surrounds a distal region of the shaft of said tube in the manner of a cuff for the purpose of sealing it against the hollow organ, wherein one or more secondary lumens for filling said intracorporeal sealing balloon are integrated into the wall of at least a proximal region of said shaft, wherein, the pressure within the intracorporeal sealing balloon is kept nearly constant in such a way that when the volume of the hollow organ changes, a corresponding amount of the filling medium flows through one or more secondary lumens, wherein, within each cross-sectional plane that is intersected perpendicularly by the local longitudinal direction of the device, the following applies for the overall interior cross-section Q1 of the primary lumen and the sum Q2 of the interior cross-sections of all secondary lumens:

$$Q2/(Q1+Q2) \geq 0.06,$$

wherein a connection for an extracorporeal filling tube, which connection communicates with all secondary lumens, is provided at a proximal end of the tube, and wherein, in said extracorporeal filling tube,
a) a one-way valve is disposed which permits a flow in case of a pressure gradient from an extracorporeal reservoir balloon, which is or can be connected to the extracorporeal filling tube, in a direction toward the intracorporeal sealing balloon, but not in the opposite direction, and
b) a flow constriction is arranged which permits only a limited flow in every flow direction,
wherein the one-way valve and the flow constriction are arranged in parallel.

17. The method according to claim 16, characterized in that the one or more secondary lumens to the intracorporeal sealing balloon are dimensioned such that, at a pressure level within a balloon system comprising the intracorporeal sealing balloon and the extracorporeal reservoir balloon of 20 to 35 mbar above atmospheric pressure, initial pressure differences within the balloon system have reduced to a residual pressure difference of 5 mbar or less, or to a residual pressure difference of 2 mbar or less, or to a residual pressure difference of 1 mbar or less after a compensation time of max. 20 ms, or after a compensation time of max. 10 ms.

\* \* \* \* \*